US012636175B2

(12) United States Patent　　　　(10) Patent No.:　US 12,636,175 B2
Hörig et al.　　　　　　　　　　　　　(45) Date of Patent:　　May 26, 2026

(54) METHOD FOR PUTTING ON AN ORTHOSIS, AND ORTHOSIS

(71) Applicant: OTTOBOCK SE & CO. KGAA, Duderstadt (DE)

(72) Inventors: Viktor Gerhard Hörig, Duderstadt (DE); Mario Koppe, Duderstadt (DE); Jonas Bornmann, Duderstadt (DE); Jose Gonzalez Vargas, Duderstadt (DE); Etienne Overdevest, Duderstadt (DE); Johannes Zajc, Duderstadt (DE); Benjamin Schirrmeister, Duderstadt (DE)

(73) Assignee: OTTOBOCK SE & CO. KGAA, Duderstadt (DE)

( * ) Notice: Subject to any disclaimer, the term of this patent is extended or adjusted under 35 U.S.C. 154(b) by 11 days.

(21) Appl. No.: 18/721,443

(22) PCT Filed: Dec. 15, 2022

(86) PCT No.: PCT/EP2022/086229
§ 371 (c)(1),
(2) Date: Jun. 18, 2024

(87) PCT Pub. No.: WO2023/117712
PCT Pub. Date: Jun. 29, 2023

(65) Prior Publication Data
US 2025/0057679 A1　　Feb. 20, 2025

(30) Foreign Application Priority Data
Dec. 21, 2021　(DE) ..................... 10 2021 134 018.7

(51) Int. Cl.
*A61F 5/01*　　　　(2006.01)

(52) U.S. Cl.
CPC .... *A61F 5/0102* (2013.01); *A61F 2005/0155* (2013.01)

(58) Field of Classification Search
CPC .................. A61F 5/0102; A61F 5/0104; A61F 2005/0155; A61F 5/05; A61F 5/0123;
(Continued)

(56) References Cited

U.S. PATENT DOCUMENTS

2021/0015650 A1 * 1/2021 Kreutel ................... A61F 5/028

FOREIGN PATENT DOCUMENTS

| DE | 202017100201 U1 | 3/2017 |
| DE | 10 2019 119 645 A1 | 1/2021 |
| DE | 10 2019 130 391 A1 | 5/2021 |

* cited by examiner

*Primary Examiner* — Ophelia A Hawthorne
(74) *Attorney, Agent, or Firm* — WCF IP

(57) ABSTRACT

The invention relates to a method for putting on an orthosis (2) with a first dimensionally stable component (4), comprising a first magnetic element (36) and a first form-fitting element (8), and a second dimensionally stable component (6), comprising a second magnetic element (14) and a second form-fitting element (12), the method comprising the following steps:
　putting the first component (4) against a part of the wearer's body so it extends along the body part,
　positioning the second component (6) on the first component (4),
wherein a magnetic attractive force acts between the first magnetic element and the second magnetic element in a first direction when the orthosis (2) is mounted, and the first form-fitting element forms a form-fitting connection with the second form-fitting element, by means of which a movement of the two components relative to each other is prevented.

9 Claims, 4 Drawing Sheets

Figures 1, 2, 3, 4:
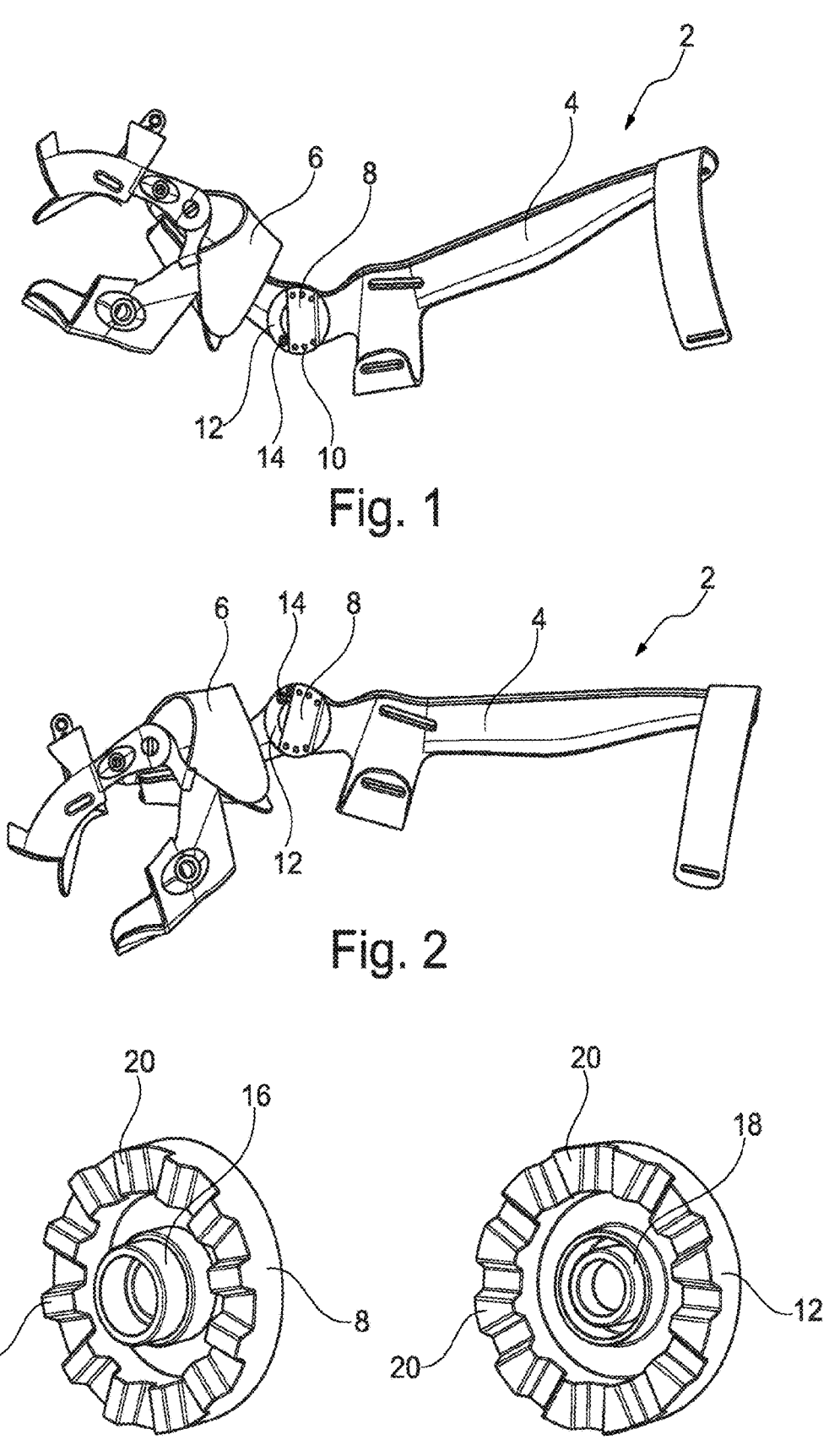

(58) Field of Classification Search
CPC ............ A61F 5/0125; A61F 2005/0132; A61F
5/0106; A61F 5/028; A61F 5/02; A61F
5/022; A61F 5/024; A61F 5/026; A61F
5/03; A61H 1/0255; A61H 1/0262; A61H
2001/0251; B25J 9/0006
See application file for complete search history.

METHOD FOR PUTTING ON AN ORTHOSIS, AND ORTHOSIS

The invention relates to a method for putting on an orthosis comprising a first dimensionally stable component and a second dimensionally stable component as well as a corresponding orthosis.

Orthoses have been known from the prior art for many years and are used to protect or support a body part, such as a joint or a limb, of a wearer of the orthosis or to limit it in an available movement range. This is advantageous, for example, following medical treatment, such as an operation, for example to protect a wearer's joint and protect it from excessive strain. The two dimensionally stable components of the orthosis are then generally arranged on the two body parts of the wearer that are connected by the joint to be protected. If, for example, this is an elbow, the first dimensionally stable component is positioned on the upper arm and the second dimensionally stable component on the lower arm.

In a different application, for example, one of the wearer's joints is to be fixed in a particular position, for example at a particular joint angle. This generally depends on the individual situation of the joint and the wearer, such that it is impossible or at least difficult for the manufacturer of the orthosis to predict. Therefore, it has been proven beneficial in the prior art if, in the case of an orthosis for this purpose, the two dimensionally stable components can be arranged and fixed in different positions relative to each other.

People who suffer a stroke, damage to the brachial plexus or comparable damage to neural structures or neural pathways often have limited motor skills in the upper limb or even experience total failure thereof. The limitations are mostly due to the lack of or insufficient enervation of the required muscles. The limb can be supported by orthoses. As a result, it is often difficult to put on such a multi-part orthosis, which comprises multiple dimensionally stable components. This applies particularly in the event that the various dimensionally stable components of the orthosis are to be positioned on different body parts, which are preferably connected by one of the wearer's joints. However, even if the orthosis is intended to enable or fix a certain position and posture of a part of the wearer's body or a joint, putting on the orthosis is associated with problems for the wearer. This is even more so the case if the position or posture is not the natural position or posture of the body part or joint.

The invention therefore aims to propose a method for putting on an orthosis that is simple and can be carried out safely, yet still guarantees sufficient security and stability of the orthosis.

The invention solves the addressed task by way of a method for putting on an orthosis with a first dimensionally stable component, comprising a first magnetic element and a first form-fitting element, and a second dimensionally stable component, comprising a second magnetic element and a second form-fitting element, the method comprising the following steps:

putting the first component against a part of the wearer's body so it extends along the body part, positioning the second component on the first component, wherein a magnetic attractive force acts between the first magnetic element and the second magnetic element when the orthosis is mounted, and the first form-fitting element forms a form-fitting connection with the second form-fitting element, by means of which a movement of the two components relative to each other is prevented.

Consequently, the first component is first put against the part of the wearer's body such that it extends along the body part. For example, the first component may be a rail or shell and is put against the part of the wearer's body and fixed, for example by means of fastening straps. In this state, the second component is not yet connected to the first component, such that, for example, a position of the two components relative to each other does not yet need to be taken into account. This makes it especially easy for the wearer of the orthosis to arrange the component on their body part.

The second component is not positioned on the first component until this has been done. Preferably, the position and/or orientation of the two components relative to each other that is necessary and sensible for the orthosis to function is adopted and fixed. In this case, the wearer of the orthosis only has to hold onto and move the second component, as the first component is already on their body part. This also reduces the degree of motor skills required for the method.

When the orthosis is mounted, a magnetic attractive force acts between the first magnetic element and the second magnetic element, which counters a first movement of the two components relative to each other. In the simplest case, the first magnetic element contains one magnet and the second magnetic element contains one magnet, wherein these magnets are positioned in relation to each other when the orthosis is mounted in such a way that the north pole of the one magnet points towards the south pole of the other magnet.

In addition to this magnetic attractive force, the first form-fitting element and the second form-fitting element form a form-fitting connection when the orthosis is mounted, by means of which a movement of the two components relative to each other is prevented. This does not necessarily mean that every movement of the two components relative to each other is prevented. While this does constitute a preferred design, it is not essential. For many applications, it is sufficient for individual movements, such as rotations about individual axes of rotation or displacements in individual displacement directions, to be prevented by the form-fitting connection. Likewise, it does not necessarily mean that only a single movement, for example the rotation about a single axis of rotation or the displacement in a single displacement direction, is prevented by way of the form-fitting connection. In preferred embodiments, for example, all displacements of the two components relative to each other are prevented, other then the displacements in a single displacement direction. This means that displacements, i.e. translational movements of the two components relative to each other, are only possible in this single direction, but are prevented by the form-fitting connection in all other directions. In one advantageous embodiment, for example, all rotations of the two components relative to each other are prevented, other then rotation about a single axis of rotation. This means that a rotation of the two components relative to each other is only possible about a single axis of rotation. The remaining rotations about all other axes of rotation are prevented by the form-fitting connection.

Due to the magnetic attractive force between the first magnetic element and the second magnetic element, all movements of the two components relative to each other for which said magnetic attractive force has to be overcome are rendered more difficult. Preferably, at least some of these movements, but preferably all of these movements, are prevented by the form-fitting connection between the two form-fitting elements.

The first magnetic element and/or the second magnetic element are preferably permanent magnets. The first magnetic element and/or the second magnetic element can also be designed as an electromagnet. To generate a magnetic attractive force, however, it is not necessary for both the first magnetic element and the second magnetic element to be magnetic themselves, i.e. to be a permanent magnet or an electromagnet. Rather, it is sufficient if just one of the magnetic elements comprises a permanent magnet or an electromagnet and the respective other magnetic element contains a magnetizable element, for example made of a ferromagnetic material.

According to the invention, each of the two dimensionally stable components has one form-fitting element and one magnetic element. The form-fitting element and/or the magnetic element can be designed as a single piece with the rest of the respective dimensionally stable component or a part thereof, for example a base body, a shell or a rail. Alternatively, the form-fitting element and/or the magnetic element can also be designed as a separate element that is connected to the rest of the respective dimensionally stable component or a part thereof, for example a base body, a shell or a rail. The form-fitting connection between the first form-fitting element and the second form-fitting element can be achieved, for example, by plugging a plug, which constitutes one of the two form-fitting elements, into a correspondingly designed socket, which constitutes the respective other form-fitting element. Such connections are sufficiently known from the prior art so that a more detailed description shall not be provided at this point.

In one embodiment example, for example, both the first dimensionally stable component and the second dimensionally stable component have a corresponding socket. These are arranged, for example, on a part thereof, such as a base body, a shell or a rail. To be able to connect the two dimensionally stable components to each other in a form-fitting manner, an adapter is preferably used which is initially connected to one of the two sockets. It becomes part of the respective dimensionally stable components as a result. It then forms the respective form-fitting element of the dimensionally stable component that can interact with the form-fitting element of the respective other dimensionally stable component and create the form-fitting connection.

The first form-fitting element and/or the second form-fitting element can be designed as a separate element that is or can be connected to the rest of the respective dimensionally stable component or a part thereof, for example a base body, a shell or a rail. The first magnetic element and/or the second magnetic element can be designed as a separate element that is or can be connected to the rest of the respective dimensionally stable component or a part thereof, for example a base body, a shell or a rail. The first magnetic element and the first form-fitting element can be designed together as a separate component. The second magnetic element and the second form-fitting element can be designed together as a separate component. These components are referred to as combined elements. The respective combined element can be designed such that it is or can be connected to the rest of the respective dimensionally stable component or a part thereof, for example a base body, a shell or a rail.

During positioning on the first component, the second component is preferably first moved closer to the first component so as to generate a magnetic attractive force. In the process, the magnetic elements are preferably arranged and configured in such a way that the magnetic attractive force pulls the second component and the first component into the desired position relative to each other. In this way, it can guide the movement of the two components relative to each other during positioning and support the wearer of the orthosis so that it is easier for them to reach the desired and required position and/or orientation of the second component relative to the first component. Consequently, the magnetic attractive force pulls the second component at least also into the desired position. In this context, the term "at least also" means that there may well be other forces that position and orientate the two components relative to each other, so that it is not only the magnetic attractive force that moves the two components relative to each other, but the magnetic attractive force is "at least also" involved.

Preferably, the form-fitting connection is not created until after positioning the second component on the first component, said connection being achieved by engaging the the first form-fitting element and the second form-fitting element. This is especially advantageous if the movement, by means of which the two components have been positioned relative to each other, is to be prevented in the opposite direction by the form-fitting connection.

Preferably, the first form-fitting element and/or the second form-fitting element are moved relative to each other to enable to the two form-fitting elements to engage with each other. Such a movement of at least one of the form-fitting elements can be carried out, for example, by the wearer of the orthosis themselves by, for example, engaging latching elements or velcro fastener elements, clip elements or other form-fitting elements with one another.

In one advantageous embodiment, the first form-fitting element and/or the second form-fitting element is moved by a force exerted by the first magnetic element and/or the second magnetic element out of a first position into a second position, thus creating the form-fitting connection. For example, this can be achieved in that the first form-fitting element and/or the second form-fitting element contains a magnet or a magnetizable element which is attracted or repelled by the magnetic field of the first magnetic element and/or the second magnetic element. This results in a movement which, for example, causes the form-fitting connection to be created.

In one specific embodiment, one of the form-fitting elements is at least one metal pin, which is arranged such that it can be displaced along its longitudinal direction in a corresponding bore in one of the two components. The corresponding other form-fitting element is designed in the form of similar bores in the other component. If, following positioning of the second component on the first component, the two components are in the desired position, in which the form-fitting connected is to be created, the at least one metal pin is displaced inside the bore along its longitudinal direction until it is partially located in the correspondingly designed bore in the other component. It now partially extends into the bores of the two components, preventing all but the longest movement along the longitudinal direction and the direction in which the bores extend. The movement itself can be caused by separate magnetic elements or by the first magnetic element and/or the second magnetic element.

In one preferred embodiment, the first form-fitting element and/or the second form-fitting element can be actuated by an actuation element. It is actuated in order to create the form-fitting connection. The corresponding form-fitting element can, for example, be pre-tensioned towards the second position, in which the form-fitting connection is created, by, for example, a spring or an elastic element exerting a corresponding force on the form-fitting element. However, so long as the actuation element is not actuated, the corresponding force cannot cause a movement of the form-fitting element, for instance because a retaining element holds the form-fitting element in the first position, in which a form-fitting connection has not yet been created. Actuating the actuation element releases said retaining element and the force applied by the spring or the elastic element moves the respective form-fitting element out of the first position into the second position, thus engaging the two form-fitting elements with one another.

Advantageously, the magnetic attractive force and the form-fitting connection are already generated during positioning of the second component on the first component. This happens, for example, if a certain movement of the components in relation to each other has to be carried out when positioning the two components against each other, for example to move the two components in relation to each other along a certain path. To this end, one of the two components features a projection, for example, which is guided along in a corresponding slot, groove or other recess or opening in the other component. This creates a form-fitting connection during positioning, which prevents many, preferably all, movements except for the movement required to position the components relative to each other. Along this movement and the path covered, the distance between the first magnetic element and the second magnetic element preferably decreases, so that the distance between unlike poles of the two magnetic elements decreases, thereby increasing the magnetic attractive force.

Preferably, the second component is also arranged on a second body part of the wearer during positioning on the first component. In this case, the first component is located on a first body part after positioning and the second component on a second body part. Preferably, the two body parts are connected to each other by a joint, such as an ankle joint, a knee, a wrist or an elbow, said joint being bridged by the orthosis.

In one preferred embodiment, the first component can be fixed on the second component in different positions and/or orientations. The magnetic elements of the two components preferably have multiple individual magnets or magnetizable elements, which are arranged and aligned in relation to each other such that an attraction force acting between them favors the positions and/or orientations of the components relative to each other in which the components can be fixed against each other. For example, the magnetic elements of the two components can each have multiple individual magnets that are arranged in different orientations on the respective component. In one preferred embodiment, the individual magnets are arranged next to each other, preferably equidistantly, on the respective component and each at an 180° offset to each other. This means that the magnetic poles of two adjacent individual magnets pointing in the same direction are unlike poles. If both magnetic elements of the two components are configured in this way, an attraction force occurs between the individual magnets positioned on the two components when unlike poles are arranged opposite each other; when like poles are positioned opposite each other, a repulsive force occurs. The same is also possible with a distribution of individual magnets around the circumference of an opening and the circumference of a projection. The opening then forms part of one of the components and the projection part of the other component. If the projection is now inserted into the opening, the individual magnets are arranged opposite each other. If this is also an alternating alignment, there is an attractive interaction between opposing individual magnets or a repulsive interaction, depending on the angular position between the projection and the opening. This also allows positions and/or orientations to be favored by the magnetic interactions.

The invention also solves the addressed task by way of an orthosis with a first component, comprising a first magnetic element and a first form-fitting element, and a second dimensionally stable component, comprising a second magnetic element and a second form-fitting element, the orthosis being configured to be put on using the method described here.

Preferably, the first magnetic element and/or the second magnetic element have multiple individual magnets, which are arranged on the respective component in different north/south orientations. This enables them to achieve the advantages described above.

Particularly preferably, the first and/or the second magnetic element has at least one magnetizable element which interacts with a magnetic element of the respective other component when mounted.

Advantageously, at least one of the magnetic elements or at least one individual magnet of one of the magnetic elements is fixed to one of the form-fitting elements. Particularly preferably, the first form-fitting element and/or the second form-fitting element can be actuated by an actuation element. Particularly preferably, the actuation element has at least one magnet.

In the following, a number of embodiment examples of the invention will be explained in more detail with the aid of the accompanying drawings.

They show:

FIGS. 1 and 2—schematic representations of an orthosis,

FIGS. 3 to 11—schematic representations of various form-fitting and magnetic elements, FIGS. 12 to 15—different stages during the connection of two elements.

FIG. 1 schematically depicts an orthosis 2 for a lower arm and a hand situated on it. The orthosis 2 has a first dimensionally stable component 4 for putting it on the lower arm and a second dimensionally stable component 6 for putting it on the hand. The first dimensionally stable component 4 has a first form-fitting element 8, which is designed as a single piece with the rest of the first dimensionally stable component 4 in the embodiment example shown. In the embodiment example shown, the first form-fitting element 8 has recesses 10 in which first magnetic elements are located, wherein said elements cannot be seen in the representation in FIG. 1. The second dimensionally stable component 6 has a second form-fitting element 12 on which second magnetic elements 14 are located, of which one is depicted. In FIG. 1, the form-fitting elements 8, 12 and the magnetic elements contained therein or arranged thereon allow the two dimensionally stable components 4, 6 to be arranged in different orientations in relation to each other. FIG. 1 shows a first of these orientations.

FIG. 2 shows the same orthosis as FIG. 1. However, one recognizes that the first dimensionally stable component 4 and the second dimensionally stable component 6 are arranged in a different orientation relative to each other. This can also be seen on the two form-fitting elements 8, 12 and in particular the second magnetic element 14, of which different ones are recognizable in FIG. 2 than was the case in the situation in FIG. 1. In relation to the representation in FIG. 1, the first dimensionally stable component 4 and the second dimensionally stable component 6 are shown as having been swivelled about a swivel axis and fixed to each other, said axis protruding out of a drawing plane.

FIGS. 3 and 4 depict a first form-fitting element 8 and a second form-fitting element 12, which are designed correspondingly to one another. The first form-fitting element 8 depicted in FIG. 3 has a projection 16 that has a circular cross-section and protrudes from an end face of the first form-fitting element 8. Correspondingly, the second form-fitting element 12 in FIG. 4 depicts an annular groove 18, which is designed in such a way that the projection 16 of the first form-fitting element 8 can be accommodated in it. The groove 18 and the projection within it prevents the two form-fitting elements 8, 12 from tilting relative to each other.

Both the first form-fitting element 8 and the second form-fitting element 12 have a face toothing 20, comprising multiple teeth distributed across the circumference. The two face toothings 20 are designed correspondingly to each other. If the two form-fitting elements 8, 12 are connected to each other, as shown in FIGS. 3 and 4, the projection 16 of the first form-fitting element 8 is first inserted into the specially provided groove 18 of the second form-fitting element 12. This results in a centering of the two form-fitting elements relative to each other. In this state, the two form-fitting elements 8, 12 can only be twisted or rotated in relation to each other, the respective axis of rotation being the longitudinal axis of the projection 16. If the two form-fitting elements 8, 12 are moved further towards each other, the two face toothings 20 come into contact with one another and engage. From this point onwards, a rotation about the specified axis of rotation is no longer possible. However, this embodiment still allows the two form-fitting elements 8, 12 to be fixed relative to each other in different orientations.

In a preferred embodiment, magnetic elements are already arranged on the two form-fitting elements 8, 12; however, the former are not depicted in FIGS. 3 and 4. For example, individual magnets can be arranged in the depressions between two adjacent teeth of the face toothings 20. In this case, different arrangements are conceivable. The individual magnets can be arranged in the same direction in the first form-fitting element 8 and on the second form-fitting element 12. This means that the individual magnets are all arranged on the first form-fitting element 8 in such a way that their north pole or south pole protrudes out of the end face. In the same way, the individual magnets in this case are preferably arranged on the second form-fitting element 12 such that their south pole or their north pole protrudes out of the end face. In this case, an attractive magnetic interaction is generated whenever the two form-fitting elements 8, 12 are moved closer to each other.

Alternatively, the individual magnets can also be arranged in the two form-fitting elements 8, 12 in an alternating manner, so that an individual magnet whose north pole projects out of the respective end face is next to two individual magnets whose south pole protrudes out of the end face. As a result, an attractive interaction is only generated in a few orientations of the two form-fitting elements relative to each other.

Figures 5, 6, 7, 8, 9, 10, 11:
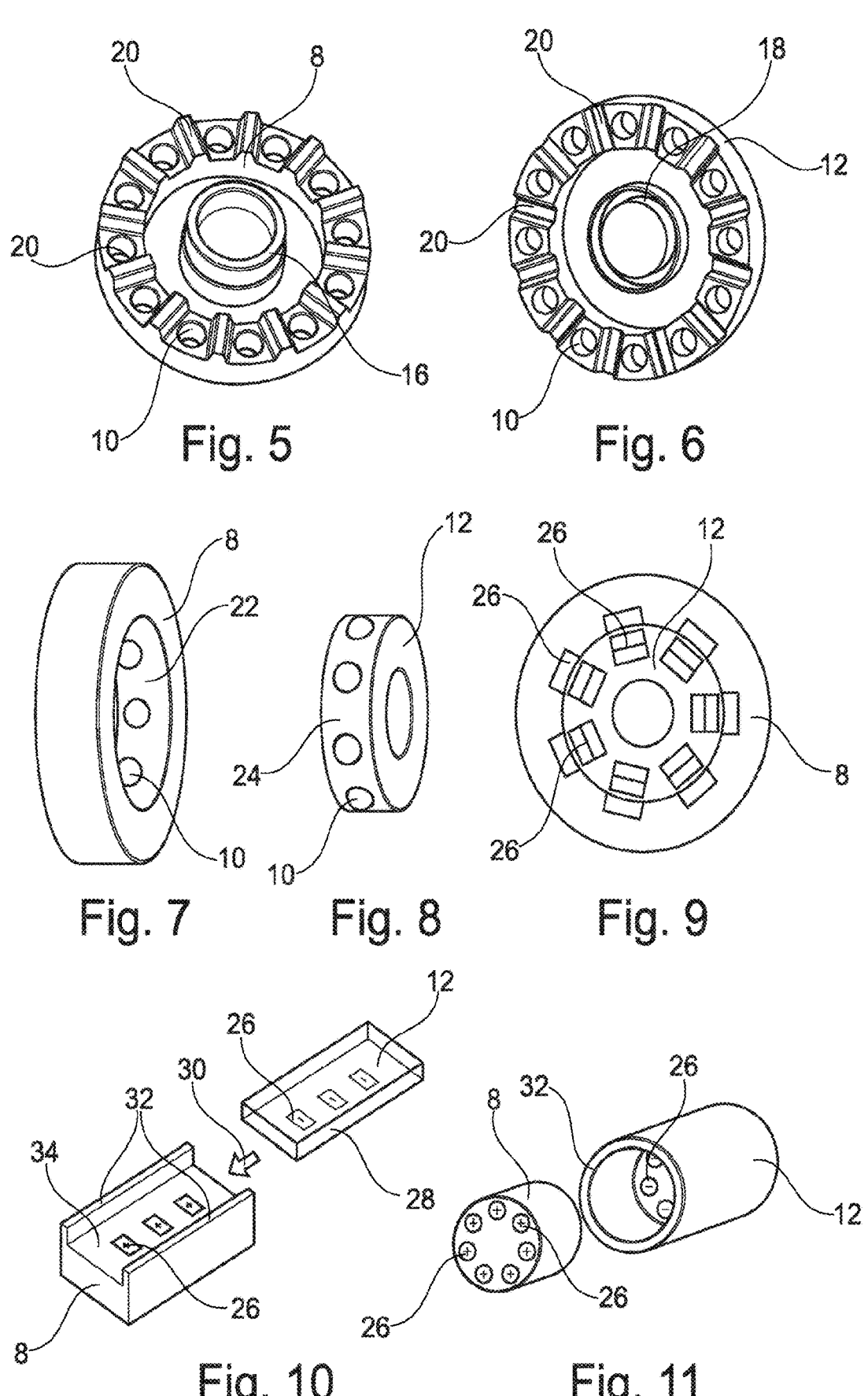
Figure 12:
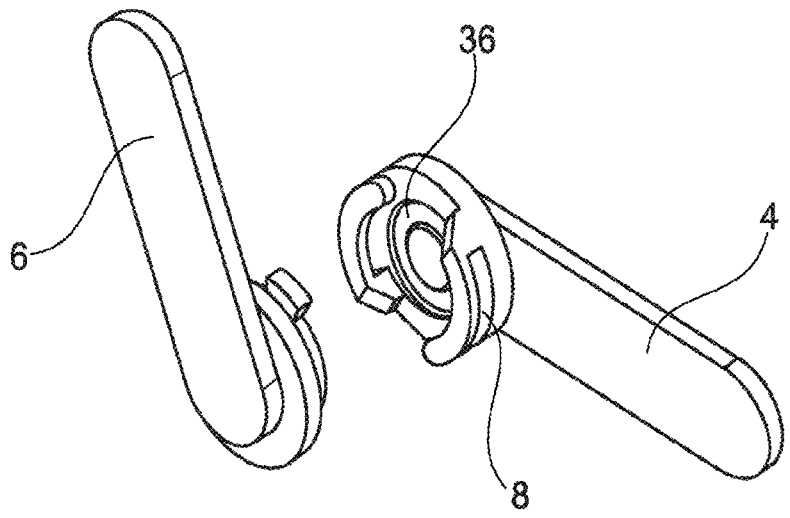

FIGS. 5 and 6 depict similar form-fitting elements 8, 12 as FIGS. 3 and 4. In this case too, the first form-fitting element 8 has the projection 16 and the second form-fitting element 12 the corresponding groove 18. The face toothings 20 are also provided in both form-fitting elements 8, 12. The first form-fitting element 8 features protruding teeth, while the second form-fitting element 12 has corresponding depressions. Recesses 10, in which individual magnets can be arranged, are arranged between the respective teeth and depressions.

FIGS. 7, 8 and 9 schematically depict a further embodiment example of the two form-fitting elements 8, 12. The first form-fitting element 8 depicted in FIG. 7 is designed to be annular and on its inner side 22 features the recesses 10 in which the non-depicted magnetic elements or individual magnets can be arranged. The inner diameter of the first form-fitting element 8 corresponds to the outer diameter of the second form-fitting element 12 shown in FIG. 8. On the outer side 24 of the latter are the recesses 10 for the individual magnets or magnetic elements. If the second form-fitting element 12 as it is depicted in FIG. 8 is now inserted into the first form-fitting element 8 as it is depicted in FIG. 7, the magnetic elements or individual magnets located in the recesses 10 of the two form-fitting elements 8, 12 are moved closer together and a magnetic interaction takes place. This is schematically depicted in FIG. 9. The second form-fitting element 12 is arranged within the first form-fitting element 8. Individual magnets 26 are schematically depicted, which are arranged in the recesses 10 of the two form-fitting elements 8, 12 and are now aligned such that they interact magnetically with each other.

FIG. 10 shows a different embodiment of the form-fitting elements. The second form-fitting element 12 is designed as a cuboid, on the lower side 28 of which 3 individual magnets 26 are arranged in the embodiment example shown. The first form-fitting element 8 is designed such that the second form-fitting element 12 can be inserted along the arrow 30 between two limits 32. In this position, the limits 32 prevent a movement of the two form-fitting elements 8, 12 transverse to the direction of the arrow 30, so that a partial form-fit occurs. Individual magnets 26 are also arranged between the two limits 32 on the upper side 34 of the form-fitting element 8.

In FIG. 11, the first form-fitting element 8 is designed to be cylindrical and has individual magnets 26 on an end face, which are arranged identically in the embodiment example shown. This means that for all individual magnets 26 shown, the south pole, characterized by a "+", points out of the end face. The second form-fitting element 12 has an annular limit 32 at its end face. The inner diameter of this ring corresponds to the outer diameter of the first form-fitting element 8, so that it can be inserted into the limit 32 rotated by 180°. The second form-fitting element 12 also has individual magnets 26, which are arranged identically to one another, on the end face located in it.

FIGS. 12 to 15 show various phases during the connection of the first dimensionally stable component 4 to the second dimensionally stable component 6. The first dimensionally stable component 4 has a first magnetic element 36 in the form of a magnetic ring. It also has the first form-fitting element 8 in the form of a circumferential slot. The second dimensionally stable component 6 comprises the second magnetic element 14, which it not visible in FIG. 12. It is also designed in the form of a magnetic ring and corresponds to the first magnetic element 36 of the first dimensionally stable component 4. The second form-fitting element 12 is designed in the form of two projections, only one of which is visible in FIG. 12. To connect the two dimensionally stable components 4, 6, the two components 4, 6 are moved closer to each other, thereby creating an attractive force between the two magnetic elements 36, 14.

Figure 13:
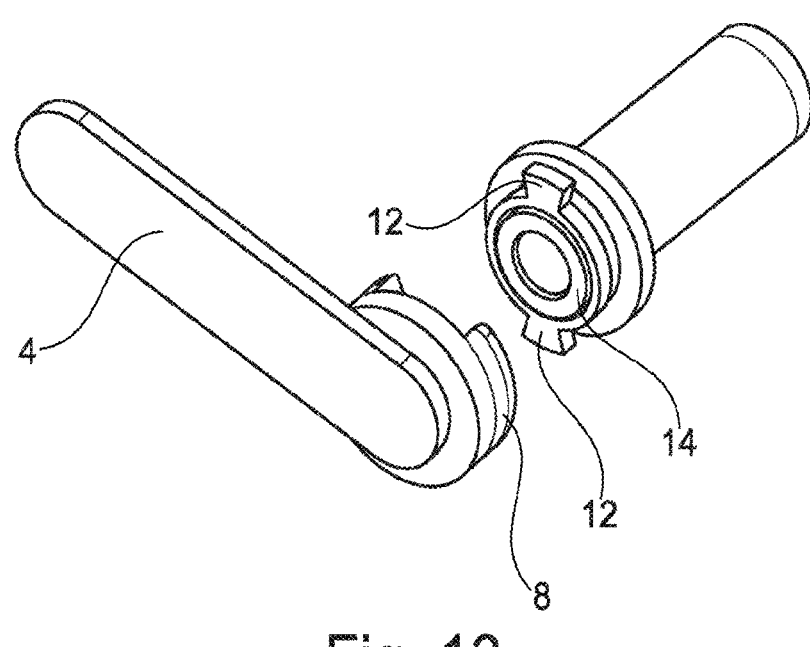

FIG. 13 shows the situation from a different perspective. Here, the two projections of the second form-fitting element 12 as well as the second magnetic element 14 are easily recognizable.

Figure 14:
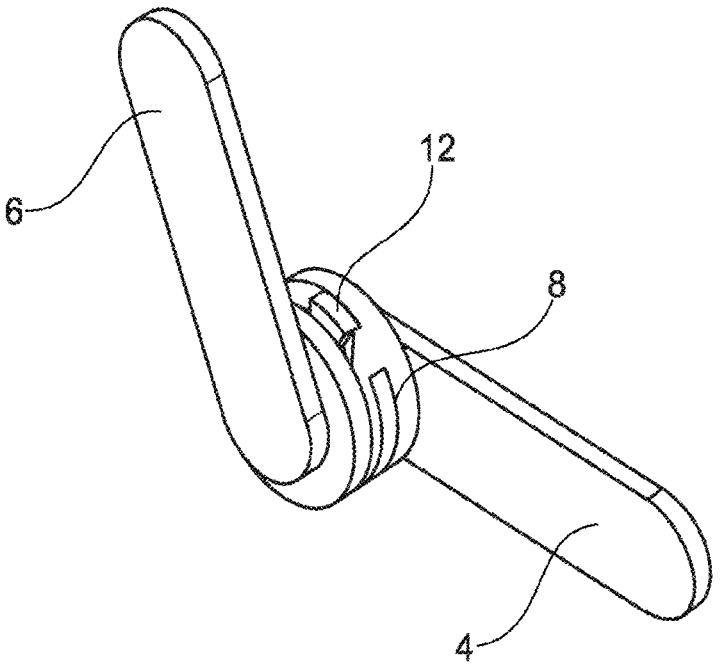
Figure 15:
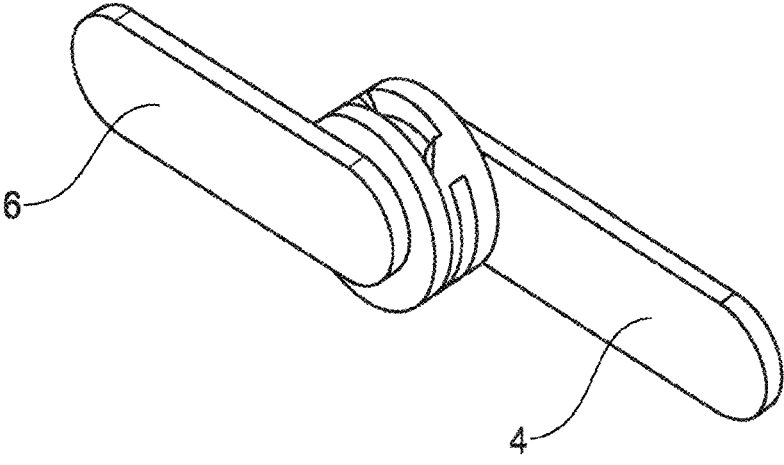

In the position shown in FIG. 14, the former are arranged so close together that the projections of the second form-fitting elements 12 engage in the slot of the first form-fitting element. They can then be moved towards each other in the manner of a bayonet lock by turning the two dimensionally stable components 4, 6 relative to each other. This situation is shown in FIG. 15.

REFERENCE LIST

2 orthosis
4 first dimensionally stable component
6 second dimensionally stable component
8 first form-fitting element
10 recess
12 second form-fitting element
14 second magnetic element
16 projection
18 groove
20 face toothing
22 inner side
24 outer side
26 individual magnets
28 lower side
30 arrow
32 limit
34 upper side
36 first magnetic element

The invention claimed is:

1. A method for putting on an orthosis, wherein the orthosis comprises
  a first dimensionally stable component comprising a first magnetic element and a first form-fitting element, and
  a second dimensionally stable component comprising a second magnetic element and a second form-fitting element, comprising:
putting the first dimensionally stable component against a part of a wearer's body so the first dimensionally stable component it extends along a body part; and
positioning the second dimensionally stable component on the first dimensionally stable component,
  wherein a magnetic attractive force acts between the first magnetic element and the second magnetic element in a first direction when the orthosis is mounted, and
  wherein the first form-fitting element forms a form-fitting connection with the second form-fitting element such that a movement of the first form-fitting element and the second form-fitting element relative to each other is prevented.

2. The method according to claim 1 further comprising engaging the first form-fitting element and the second form-fitting element after the step of positioning the second dimensionally stable component on the first dimensionally stable component.

3. The method according to claim 2, further comprising the step of moving the first form-fitting element and/or the second form-fitting element relative to each other.

4. The method according to claim 3, wherein the first form-fitting element and/or the second form-fitting element is or are moved by a force exerted by the first magnetic element and/or the second magnetic element, wherein the force moves the first form-fitting element and/or the second form-fitting element out of a first position into a second position, thus creating the form-fitting connection.

5. The method according to claim 1, wherein the step of positioning the second dimensionally stable component on the first dimensionally stable component comprises initially moving the second dimensionally stable component closer to the first dimensionally stable component so as to generate an attraction force, wherein the attraction force pulls the second dimensionally stable component into an attracted a position.

6. The method according to claim 1 further comprising the step of actuating the first form-fitting element and/or the second form-fitting element by an actuation element to create the form-fitting connection.

7. The method according to claim 1 wherein the magnetic attractive force and the form-fitting connection are generated during positioning of the second dimensionally stable component on the first dimensionally stable component.

8. The method according to claim 1 the second dimensionally stable component is arranged on a second part of the wearer's body during positioning the second dimensionally stable component on the first dimensionally stable component.

9. The method according to claim 1 further comprising fixing the first dimensionally stable component on the second dimensionally stable component in one or more positions and/or orientations.

* * * * *